US008399398B2

(12) United States Patent
Smith

(10) Patent No.: US 8,399,398 B2
(45) Date of Patent: Mar. 19, 2013

(54) ORGANOLEPTIC COMPOUNDS AND THEIR USE IN PERFUME COMPOSITIONS

(75) Inventor: Catherine Marie Smith, Bayville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/282,864

(22) Filed: Oct. 27, 2011

(65) Prior Publication Data

US 2012/0041077 A1 Feb. 16, 2012

Related U.S. Application Data

(62) Division of application No. 11/464,403, filed on Aug. 14, 2006, now Pat. No. 8,071,530.

(51) Int. Cl.

| | |
|---|---|
| ***A61K 8/18*** | (2006.01) |
| ***A61K 8/00*** | (2006.01) |
| ***A61Q 13/00*** | (2006.01) |
| ***C07C 41/00*** | (2006.01) |
| ***C07C 43/00*** | (2006.01) |
| ***C07C 43/02*** | (2006.01) |
| ***C07C 43/20*** | (2006.01) |

(52) U.S. Cl. ................ 512/25; 512/1; 512/20; 568/579; 568/626

(58) Field of Classification Search .................. 568/579, 568/626; 512/1, 20, 25

See application file for complete search history.

(56) References Cited

U.S. PATENT DOCUMENTS 3,410,723 A * 11/1968 Cohz .......................... 134/22.16
4,517,388 A * 5/1985 Braverman ................... 568/779

OTHER PUBLICATIONS

Perrott et al. (Canadian Journal of Chemistry vol. 75 pp. 384-397 1997).*
Chapman and Hall (Dictionary of Organic Compounds 6th ed., vol. 5, 1996 New York) p. 5213.*

* cited by examiner

*Primary Examiner* — Patrick Ryan
*Assistant Examiner* — Aaron Greso
(74) *Attorney, Agent, or Firm* — Elizabeth M. Quirk; XuFan Tseng; Joseph F. Leightner

(57) ABSTRACT

The present invention a method of improving, enhancing or modifying a fragrance formulation through the addition of an olfactory acceptable amount of the following compound:

Formula I

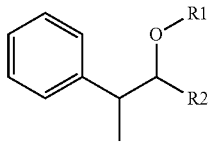

wherein $R^1$ and $R^2$ independently represent a straight, branched or cyclic hydrocarbon moiety consisting of less than 10, preferably less than 4, most preferably 1 of 2 carbon atoms.

19 Claims, No Drawings

ORGANOLEPTIC COMPOUNDS AND THEIR USE IN PERFUME COMPOSITIONS

STATUS OF RELATED APPLICATIONS

This application is a divisional of U.S. Ser. No. 11/464,403, filed Aug. 14, 2006, now U.S. Pat. No. 8,071,530 now allowed, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like.

More specifically, the present invention is directed to novel fragrance compounds and a method of improving, enhancing or modifying a fragrance formulation through the addition of an olfactory acceptable amount of such fragrance compounds represented by Formula I set forth below:

Formula I

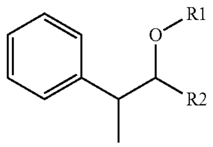

wherein $R^1$ and $R^2$ independently represent a straight, branched or cyclic hydrocarbon moiety consisting of less than 10, preferably less than 4, most preferably 1 to 2 carbon atoms.

Another embodiment of the invention is directed to a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formulae I above, $R^1$ and $R^2$ independently represent hydrogen or a straight, branched or cyclic hydrocarbon moiety consisting of less than 15, preferably less than 10, most preferably less than 4 carbon atoms. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable hydrocarbon moieties containing double bonds include ethene, propene, 1-butene, 2-butene, penta-1-3-deine, hepta-1,3,5-triene and the like.

In another embodiment of the invention, the novel compounds of the invention are represented by the following structures:

Structure I

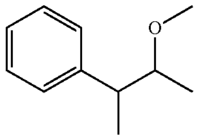

Structure II

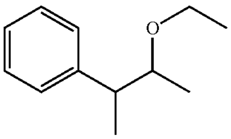

Structure III

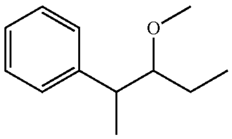

Structure IV

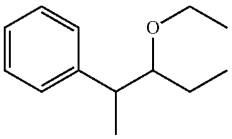

Those with the skill in the art will appreciate that:

Structure I is (2-methoxy-1-methylpropyl)-benzene;

Structure II is (2-ethoxy-1-methylpropyl)-benzene;

Structure III is (2-methoxy-1-methylbutyl)-benzene; and

Structure IV is (2-ethoxy-1-methylbutyl)-benzene.

The compounds of the present invention may be prepared from the corresponding alcohols via ether formation of the following sequence:

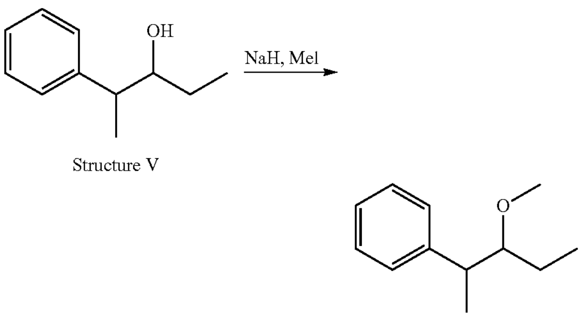

Structure V

Structure III wherein Structure V represents 2-phenyl-pentan-3-ol (commercially available from Aldrich Chemical Company);

NaH represents sodium hydride;

MeI represents iodomethane; and

Structure III is defined as above.

Structure V in the above scheme was also prepared according to the procedure described in Shumway, W.; Ham, S.; Moer, J.; Whittlesey, B.; Birney, D. (*J. Org. Chem.* 2000, 65, 7731).

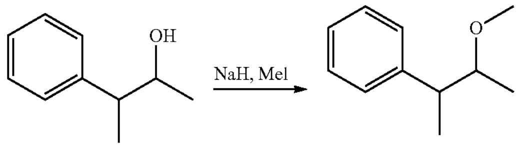

Structure VI Structure I wherein Structure VI represents 3-phenyl-butan-2-ol; and NaH, MeI, and Structure I are defined as above.

Structure VI in the above scheme was prepared according to the procedure described in Alverez-Ibarra, C.; Arjona, O.; Perez-Ossorio, R.; Perez-Rubalcaba, A.; Quiroga, M.; Santesmases, M. (*J. Chem. Perkin Trans.* 2 1983, 11, 1645).

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products as well as fabric care product, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The compounds of the present invention are surprisingly found to possess strong and unexpected fragrance effect such as, for example, floral, green, fruity, woody, wasabi, grapefruit, citrus, fresh, khusinil, and spicy notes.

When used in a fragrance formulation, the compounds of the present invention provide freshness and make the fragrance top notes more desirable and noticeable. It also has spicy peppery properties that are commonly used in men's fragrances, which add fragrance appropriateness and desirability. The woody note is very useful in both men's and women's fragrances that adds body and substantivity to the finished products. The floral note makes the fragrance more desirable and adds the perception of value. The fruity property can be found in many fragrances today. This character is very trendy, and is especially desired by younger consumers. In sum, the odor qualities found in the compounds of the present invention assist in beautifying and enhancing the finished accord and in improving the performance of other materials in the fragrance.

The following are provided as specific embodiments of the present invention. Other modifications of this invention will be readily apparent to those skilled in the art. Such modifications are understood to be within the scope of this invention. All reagents were purchased from Sigma-Aldrich, Inc. unless otherwise noted. As used herein all percentages are weight percent unless otherwise noted, ppm is understood to stand for parts per million, g is understood to be grams, L is understood to be liter, mL is understood to be milliliter, mol is understood to be mole, DMF stands for dimethylformamide, and $NH_4Cl$ stands for ammonium chloride. IFF as used in the examples is understood to mean International Flavors & Fragrances Inc., New York, N.Y., USA.

Example I

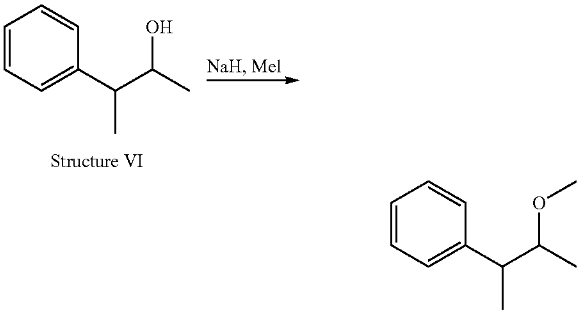

Structure VI

Structure I

Preparation of (2-methoxy-1-methylpropyl)-benzene (Structure I): A 2 L reaction flask was charged with NaH (32 g, 0.79 mol) in oil dispersion (60%) and DMF (500 mL) under $N_2$. The mixture was heated to 40° C. 3-Phenyl-butan-2-ol (100 g, 0.66 mol) was fed to the mixture over 1 hour. The reaction mixture was aged for 1 hour at 40° C. Iodomethane (113 g, 0.79 mol) was then fed into the reaction mixture over 2 hours. The reaction mixture was further aged for 8 hours, and quenched subsequently with saturated $NH_4Cl$ solution (300 mL). The layers were separated. The organic layer was washed with saturated $NaHCO_3$ (300 mL) and brine (300 mL) to provide a crude product, which was purified by distillation to afford (2-methoxy-1-methylpropyl)-benzene (101 g, 61% yield).

$^1H$ NMR (500 MHz, $CDCl_3$) δ: 7.34-7.17 (m, 5H), 3.35 (s, 3H), 3.42-3.3.30 (m, 1H), 2.78-2.58 (m, 1H), 1.32 (d, J=7.00 Hz, 3H), 0.97 (d, 3H).

(2-Methoxy-1-methylpropyl)-benzene was described as having floral, green, fruity, and wasabi fragrance notes.

Example II

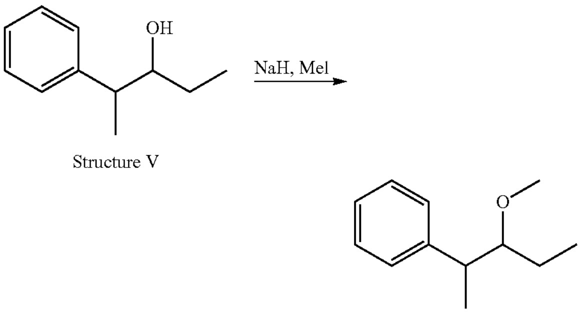

Structure V

Structure III

Preparation of (2-methoxy-1-methylbutyl)-benzene (Structure III): A 2 L reaction flask was charged with NaH (29.5 g, 0.73 mol) in oil dispersion (60%) and DMF (500 mL) under $N_2$. The mixture was heated to 40° C. 2-Phenyl-pentan-3-ol (100 g, 0.61 mol) was fed to the mixture over 1 hour. The reaction was aged for 1 hour at 40° C. Iodomethane (103 g, 0.73 mol) was then fed into the reaction mixture over 2 hours.

The reaction mixture was further aged for 8 hours, and quenched subsequently with saturated $NH_4Cl$ solution (300 mL). The layers were separated. The organic layer was washed with saturated $NaHCO_3$ (300 mL) and brine (300 mL) to provide a crude product, which was purified by distillation to afford (2-methoxy-1-methylbutyl)-benzene (63 g, 58% yield).

$^1H$ NMR (500 MHz, $CDCl_3$) δ: 7.34-7.17 (m, 5H), 3.34 (s, 2.25H), 3.28 (s, 0.75H), 3.20-3.13 (m, 1H), 2.97 (p, J=6.77 Hz, 0.25H), 2.84 (p, J=6.99 Hz, 0.75H), 1.49-1.40 (m, 1.5H), 1.30 (d, J=7.00 Hz, 2.25H), 1.25 (d, J=7.14 Hz, 0.75H), 1.35-1.23 (m, 0.5H), 0.89 (t, J=7.47 Hz, 0.75H), 1.85 (t, J=7.40 Hz, 2.25H).

(2-Methoxy-1-methylbutyl)-benzene was described as having green, floral, grapefruit, citrus, fruity, fresh, khusinil, and spicy fragrance notes.

Example III

The fragrance formula exemplified as follows demonstrated the fragrance function of (2-methoxy-1-methyl-butyl)-benzene, which provided additional green, floral, grapefruit, citrus, fruity, fresh, khusinil, and spicy notes:

| Ingredients | Parts (g) |
|---|---|
| Aldehyde AA Triplal BHT | 5.00 |
| Allyl Amyl Glycolate | 10.00 |
| Amyl Sal | 15.00 |
| Benz Acet | 60.00 |
| Citronellol Couer | 15.00 |
| Citronellol Acet | 40.00 |
| Cyclamal Extra | 20.00 |
| Ethyl Linalool | 70.00 |
| Ionone Alpha | 10.00 |
| Ionone Beta Extra | 40.00 |
| Iso Gamma Super BHT | 50.00 |
| Kharismal | 20.00 |
| Lilial | 100.00 |
| Linalool Syn | 80.00 |
| Meth Ionone Gamma Coeur | 25.00 |
| Nebulone (Elinics) | 20.00 |
| Neryl Acet A | 40.00 |
| Orange Oil Fla Decol K-10930-01 | 75.00 |
| "PFG" BHT | |
| Phen Eth Alc White Extra | 100.00 |
| Sanjinol BHT | 5.00 |
| Terpineol Coeur | 55.00 |
| Undecalactone Gamma | 30.00 |
| Verdox | 55.00 |
| (2-Methoxy-1-methylbutyl)-benzene | 60.00 |
| Total Weight | 1000.00 |

What is claimed is:

1. A method of enhancing a fragrance formulation through the addition of an olfactory acceptable amount of the following compound:

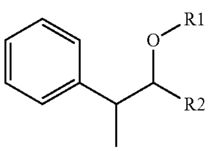

wherein $R^1$ and $R^2$ independently represent a straight, branched or cyclic hydrocarbon moiety consisting of less than 4 carbon atoms and containing single and/or double bonds.

2. The method of claim 1, wherein $R^1$ and $R^2$ independently represent a hydrocarbon moiety consisting of 1 or 2 carbon atoms.

3. The method of claim 1, wherein the compound is (2-methoxy-1-methylpropyl)-benzene.

4. The method of claim 1, wherein the compound is (2-ethoxy-1-methylpropyl)-benzene.

5. The method of claim 1, wherein the compound is (2-methoxy-1-methylbutyl)-benzene.

6. The method of claim 1, wherein the compound is (2-ethoxy-1-methylbutyl)-benzene.

7. The method of claim 1, wherein the olfactory acceptable amount is from about 0.005 to about 10 weight percent of the fragrance formulation.

8. The method of claim 1, wherein the olfactory acceptable amount is from about 0.5 to about 8 weight percent of the fragrance formulation.

9. The method of claim 1, wherein the olfactory acceptable amount is from about 1 to about 7 weight percent.

10. A fragrance formulation containing an olfactory acceptable amount of a compound of formula:

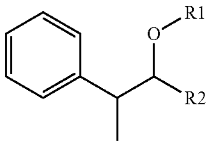

wherein $R^1$ and $R^2$ independently represent a straight, branched or cyclic hydrocarbon moiety consisting of less than 4 carbon atoms and containing single and/or double bonds, wherein the fragrance formulation possesses a floral, green, fruity, woody, wasabi, grapefruit, citrus, fresh, khusinil, or spicy note.

11. The fragrance formulation of claim 10, wherein $R^1$ and $R^2$ independently represent a hydrocarbon moiety consisting of 1 or 2 carbon atoms.

12. The fragrance formulation of claim 10, wherein the compound is (2-methoxy-1-methylpropyl)-benzene.

13. The fragrance formulation of claim 10, wherein the compound is (2-ethoxy-1-methylpropyl)-benzene.

14. The fragrance formulation of claim 10, wherein the compound is (2-methoxy-1-methylbutyl)-benzene.

15. The fragrance formulation of claim 10 incorporated into a product selected from the group consisting of a perfume, a cologne, toilet water, a cosmetic product, a personal care product, a fabric care product, a cleaning product, and an air freshener.

16. The fragrance formulation of claim 15, wherein the cleaning product is selected from the group consisting of a detergent, a dishwashing composition, a scrubbing compound, and a window cleaner.

17. The fragrance formulation of claim 10, wherein the olfactory acceptable amount is from about 0.005 to about 10 weight percent of the fragrance formulation.

18. The fragrance formulation of claim 10, wherein the olfactory acceptable amount is from about 0.5 to about 8 weight percent of the fragrance formulation.

19. The fragrance formulation of claim 10, wherein the olfactory acceptable amount is from about 1 to about 7 weight percent of the fragrance formulation.

* * * * *